US006620599B1

(12) United States Patent
Chattopadhyay et al.

(10) Patent No.: US 6,620,599 B1
(45) Date of Patent: Sep. 16, 2003

(54) PROCESS FOR THE PRODUCTION OF A BIOLOGICALLY ACTIVE PHENOLIC COMPOUND(+) CATECHIN

(75) Inventors: Sunil Kumar Chattopadhyay, Lucknow (IN); Suchitra Banerjee, Lucknow (IN); Shipra Agarwal, Lucknow (IN); Manish Kulshrestha, Lucknow (IN); Ram Prakash Sharma, Lucknow (IN); Vijay Kumar Mehta, Lucknow (IN); Sushil Kumar, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/535,806

(22) Filed: Mar. 28, 2000

(51) Int. Cl.$^7$ .................................................. C12P 17/02
(52) U.S. Cl. ....................... 435/123; 435/119; 435/118; 435/117; 435/155
(58) Field of Search ................................ 435/119, 118, 435/117, 123, 155

(56) References Cited

U.S. PATENT DOCUMENTS 4,906,656 A * 3/1990 Laks ........................... 514/456

OTHER PUBLICATIONS

Chattopadhyay et al., Chattopadhyay, S.K., et al., Indian J. Chem., Sect B: Org. Chem. Incl. Med. chem. (1999), vol. 38B(2), pp. 246–247.*
Banergee et al., Planta Medica (1996), 62(4), 333–335.*
Sigma Plant Cell Culture Catalogue, 1991–92, pp. 7–11.*
F. Trotin et al., "Flavanol production of *fagopyrum esculetum* hairy and normal root cultures," *Phytochemistry*, vol. 32, No. 4, pps. 929–931, 1993.
Kahn Ono et al., "Catechin production in cultured *poygonum hydropiper* cells," *Phytochemistry*, vol. 49, No. 7, pps. 1935–1938, 1998.
T. Bahorun et al., "Comparative polyphenolic productions in *crataegus monegyna* callus cultures," *Phytochemistry*, vol. 3y7, No. 5, pps. 1273–1276, 1994.
Y. Moumou et al., "Catechin production by callus cultures of *Fogopyrum esculentum*", *Phytochemistry*, vol. 31, No. 4, pps. 1239–1241, 1992.
Mondher Jaziri et al., "*Taxus* sp. Cell, tissue and organ cultures as alternative sources for taxoids production: a literature survey," *Plant Cell, Tissue and Organ Culture* 46:59–75, 1996.
Eckhard Wollenweber et al., "Occurrence and distribution of free flavonoid aglycones in plants," *Phytochemistry*, vol. 20, No. 5, pps. 869–932, 1981.
S. Jha et al., "Improved Taxol Yield in Cell Suspension Culture of Taxus wallichiana (Himalayan Yew)," *Plant Medica*, vol. 64, pps. 270–272, 1998.
Khoon–Huat Law et al., "Production of(–) Epicatechin by Uncaria Elliptica Callus Cultures," *Phytochemistry*, vol. 28, No. 4, pps. 1099–1100, 1989.

* cited by examiner

*Primary Examiner*—Irene Marx
(74) *Attorney, Agent, or Firm*—Jenkens & Gilchrist

(57) ABSTRACT

The invention provides a process for the production of a biologically active phenolic compound (+) catechin from *Taxus wallichiana* tissue cultures, said process comprising the steps of (a) inoculating the of explants on a culture medium supplemented with combinations of auxins and cytokinins, (b) incubating the cultures under continuous light or dark conditions for 4–6 weeks for callus initiation followed by subculturing at 4–6 weeks intervals, (c) extracting the fresh pulverized calli with polar solvents at room temperature; (d) evaporating the solvent to obtain a residue; and (e) treating the residue with a chlorinated solvent and isolating (+) catechin compound by filtration.

18 Claims, No Drawings

PROCESS FOR THE PRODUCTION OF A BIOLOGICALLY ACTIVE PHENOLIC COMPOUND(+) CATECHIN

FIELD

The present invention relates to a process for the production of a biologically active phenolic compound (+) catechin of formula 1 from *Taxus wallichiana* tissue cultures:

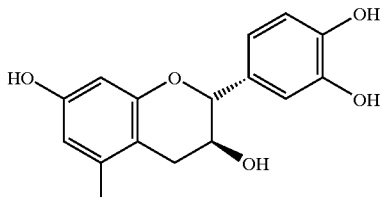

Structure of Catechin

BACKGROUND

In recent years, different Taxus species have attracted world wide attention due to the presence of taxol or its analogues in the bark or needles of the trees. Taxol, a highly oxygenated diterpenoid molecule and a potent anticancer drug was first isolated from the stem bark of *Taxus brevifolia*. Thereafter, it has also been isolated from other Taxus species including *Taxus wallichiana*.

Catechins, the basic structural unit of condensed tannins, belong to flavan-3-ol derivatives and are found in a wide variety of plant sources such as vegetables, herbs and teas (Phytochem (1981) 20:869). Considerable interest has been expressed regarding the various pharmacological functions of catechins, which have been proved to be antibacterial, antiviral, anti-tumour, antioxidant and radical scavengers (Phytochem (1998) 49:2379–82).

The direct manipulation of plant cell and tissue culture systems has resulted in an enhanced production of various secondary metabolites. In vitro production of catechins, mainly (−) epicatechin-3-O-gallate accompanied by (+) catechin and (−) epicatechin have been reported in *Fagophyrum esculentum* calli and hairy root cultures (Phytochem (1992) 31:1239–1241, Phytochem (1993) 32:929 suspension cultures of *Camellia sinensis* (ChayeKexue (1995) 15:111–116) and *Vitis vinifera* (Biotech Lett. (1996) 18:659–662), *Crataegus monogyna* (Phytochem (1994) 37:1273), *Uncaria elliptica* (Phytochem (1998) 28:1099–1 100) and *Polygonum hydropiper* (Phytochem (1998) 49:1935–39).

Several approaches have been used for the establishment of in vitro cultures of various Taxus species (Plant Cell, Tissue and Organ Cult (1996) 46:59–75). Different explants and various basal media have been used for the initiation and maintenance of Taxus callus and cell suspension cultures. The culture media are frequently supplemented with organic substances, such as casein hydrolysate, polyvinylpyrrolidone, ascorbic acid and others. Several growth regulators are used for stimulation of cell proliferation. *Taxus wallichiana*, known as Himalayan yew is available in India. Suspension and callus cultures of *Taxus wallichiana* are found capable of producing taxol (Planta Med. (1998) 64:270–72) and some important taxanes, namely 2-deacetoxy-taxinine J and 2-deacetoxy austrospicatin (Planta Med. (1996) 62:333–35). The Applicants have been screening different callus lines of *Taxus wallichiana* induced from different explants of trees collected from different geographical regions of India. The protocol standardized for in vitro callus production is dependent on media composition (viz. Murashige and Skoog's, Gambrog's, White's, Nitsch and Nitsch's), hormonal regime combinations of different concentrations of cytokinins and auxins, (such as 6-benzyl aminopurine, TDZ, 2-ip, Kinetin, 6-methylamino purine, Zeatin with NAA, IAA, IBA, 2,4-D, 2,4-T, Picloram), explant source (preferably from needles, twigs, stems devoid of needles and seeds) and culture conditions (light or dark conditions).

The callus line developed from a specific explant on different media compositions having definite hormonal combinations resulted in the production of a phenolic compound. The compound, having a molecular formula of $C_{15}H_{14}O_6$, mp 94–95° C., was isolated as an amorphous solid. The compound has been characterized as (+) catechin. The yield was noted to be 0.3% in six months old callus. The (+) catechin is very important precursor for the synthesis of other catechin derivatives, eg. Gallocatechin, epigallocatechin and epigallocatechin-3-O-gallate. It is worth mentioning here that most of the earlier reports of in vitro catechin production revealed production of a mixture of catechins, the majority of which were (−) epicatechin, (−) eipcatechin-3-O-gallate and (−) epigallocatechin, (Phytochem (1989) 28:1099–1100, (1992) 31:1239–1241 (1993) 32:924–931, (1998) 49:1935–1939), whereas in the present invention only (+) catechin is expressed. Furthermore, in the present invention 0.3% concentration of (+) catechin has been detected in 6 months old callus while the expression of (+) catechin in *Polygonum hydropiper* occurred after one year of culture initiation (Phytochem (1998) 49(7):1935–39).

OBJECTS

Thus the main object of the present invention is to provide a process for In vitro production of a biologically active phenolic compound (+) catechin of formula I from *Taxus wallichiana* tissue cultures.

Another object of the invention is to provide a process for isolation of (+) catechin from cell cultures of *Taxus wallichiana* without the use of any cumbersome chromatographic separations.

SUMMARY

The present invention consisting of the in vitro production of (+) catechin from *Taxus wallichiana* constitute the first ever report of production of (+) catechin in the genus Taxus. Moreover, the yield of (+) catechin obtained in the invention is 0.3% which is significantly better to the so far reported ones from cell culture sources taking into consideration of the reported culture period (Phytochemistry (1998) 49(7):1935–1939).

DETAILED DESCRIPTION

Accordingly the present invention relates to a process for the production of a biologically active phenolic compound (+) catechin of formula I from *Taxus wallichiana* tissue cultures which comprises: (a) inoculation of explants on culture media supplemented with combinations of auxins (1–5 mg/l) and cytokinins (0.1–1.0 mg/l); (b) incubation of the cultures under continuous light or dark conditions for 4–6 weeks for callus initiation followed by subculturing at 4–6 weeks intervals; (c) extraction of fresh pulverized calli with polar solvents at room temperature, (d) evaporating the polar solvents to obtain a residue, and (e) treatment of the residue with a chlorinated solvent and isolation of the compound (+) catechin by filtration.

In an embodiment, the explants for induction of callus may be selected from needles, twigs, stems devoid of needles and seeds of *Taxus Wallichiana*.

In another embodiment, the culture media for callus induction and multiplication are selected from Murashige and Skoog, (1962) (MS) medium, containing the following (in mg/l)—$NH_4NO_3$ (1,650), $KNO_3$ (1,900), $CaCl_2.2H_2O$ (400), $MgSO_4.7H_2O$ (370), $KH_2PO_4$ (170), $Na_2EDTA.2H_2O$ (7.2), $FeSO_4.7H_2O$ (27.8), $MnSO_4.4H_2O$ (22.3), $ZnSO_4.7H_2O$ (8.6), $H_3BO_3$ (6.2), KI (0.83), $Na_2MoO_4.2H_2O$ (0.25), $CuSO_4.5H_2O$ (0.025), $CoCl_2.6H_2O$ (0.025), Glycine (2.0), Nicotinic acid (0.5), PyridoxineHCl (0.5), ThiamineHCl (0.1); Gamborg's; (1968) (B5) medium, containing the following (in mg/l)—$KNO_3$ (3,000), $(NH_4)_2SO_4$ (134), $MgSO_4.7H_2O$ (500), $CaCl_2.2H_2O$ (150), $NaH_2PO_4.H_2O$ (150), $MnSO_4.H_2O$ (10.0), KI (0.75), $H_3BO_3$ (3.0), $ZnSO_4.7H_2O$ (2.0), $CuSO_4$ (0.025), $NaMoO_4.2H_2O$ (0.25), $CoCl_2.6H_2O$ (0.025), $Na_2EDTA.2H_2O$ (37.2) $FeSO_4.7H_2O$ (27.8), White's (1963) medium, consisting of the following (in mg/l) —$Ca(NO_3)_2$ (142.0), $KNO_3$ (81.0), $MgSO_4.7H_2O$ (70.0), KCl (65.0), $KH_2PO_4$ (12.0), $(FeSO_4)_3$ (2.46) and Nitsch and Nitsch; (1969) medium, containing the following (in mg/l)— $NE_4NO_3$ (20.0), $KNO_3$ (950), $H_3BO_3$ (10.0), $KH_2PO_4$ (68.0), $Na_2MoO_4.2H_2O$ (0.143), $CaCl_2$ (41.5), $MgSO_4.7H_2O$ (185), $M_NSO_4.4H_2O$ (15.0), $ZnSO_4.H20$ (10.0), $CuSO_4$ (0.14), $FeSO_4$ (111.4), $Na_2EDTA$ (149), Biotin (0.05), Glycine (2.0), Nicotinic acid (5.0), Pyridoxine HCl (0.5), Thiamine HCl (0.5), Folic acid (5.0).

In yet another embodiment, the auxins may be selected from Indole acetic acid (IAA), naphthalene acetic acid (NAA), indole butyric acid (IBA), 2,4-dichlorophenoxy acetic acid (2,4-D), 2,4,6,-trichlorophenoxy acetic acid (2,4-T) and picloram within the following range (1.0–5.0 mg/l).

In still another embodiment, the cytokinins may be selected from 6-benzyl amino purine (BAP), 6-methyl aminopurine (MAP), kinetin (Kn), zeatin, thiadiazuron (TDZ) and 2-isopentenyl amino purine (2-ip) within a range of about 0.1–1 mg/l.

In still another embodiment, the cultures are incubated under continuous light of 300–3000 lux or under continuous dark conditions.

In still another embodiment, harvesting time to get maximum product may be from one month to thirty six months In still another embodiment, the polar solvents may be selected from methanol, ethanol, propanol and butanol.

In still another embodiment, the ratio of auxin and cytokinin used ranges between 6 to 20:1.

In still another embodiment, the medium may be supplemented with casein hydrolysate in an amount ranging between 100–400 mg/l.

In still another embodiment, ascorbic acid used ranges between 10–50 mg/l.

In still another embodiment, of the present invention the chlorinated solvent may be selected from chloroform and dichloromethane.

Repeated experimentations have proved that use of particular explants and specific ratio of auxins and cytokinins are the critical factors for in vitro expression of (+) catechin production.

The invention is described in detail in the examples given below which are provided to illustrate the invention and therefore should not be construed to limit the scope of the invention.

EXAMPLE 1

Needle explants of mature trees of *Taxus wallichiana* were collected from different geographical regions of India, and callus cultures were initiated on Murashige and Skoog's (MS) basal medium supplemented with 2,4-D (5 mg/l), kinetin (0.25 mg/l), ascorbic acid (40 mg/l), sucrose (3%) and agar (0.8%). The cultures were maintained at 25±2° C. under continuous light condition (3000 lux). After initiation, the callus was maintained on the same medium with sub-culturing at every 4 weeks. The calli were harvested at different growth phases and extracted with methanol (5 g/20 ml). The methanol extract was concentrated under reduced pressure to a semisolid residue. The residue was treated with chloroform with stirring to obtain solids. The solids were filtered to give (+) catechin as amorphorus solid (yield 0.3%).

EXAMPLE 2

Young twigs were collected from mature trees of *Taxus wallichiana* and inoculated on Gamborg's (B5 medium supplemented with NAA (5 mg/l), Kn 0.25 mg/l), ascorbic acid (40 mg/l), casein hydrolysate (250 mg/l) sucrose (3%) and agar (0.8%). The cultures were maintained at 25±2° C. under continuous dark condition. After initiation the callus was maintained on the same medium as well as on medium supplemented with 2,4-D and kinetin of the respective concentrations with sub-culturing at every 4 weeks interval. The calli were harvested at different growth phases and extracted with ethanol (5 g/20 ml): The ethanol extract was concentrated under reduced pressure to a semi-solid residue. The residue was treated with dichloromethane with stirring to obtain a solid. The solids were filtered to give (+) catechin as amorphous solid (yield (0.3%).

EXAMPLE 3

Suspension cultures were raised from the callus initiated on B5 solid medium supplemented with NAA (1–5 mg/l) and kinetin (0.1–1.0 mg/l). These cultures were grown and maintained in MS liquid medium supplemented with similar hormonal combinations, incubated on rotary shaker at 100–120 rpm under dark conditions. The suspensions were harvested at different growth phases. For the chemical analysis, cell suspension was filtered through celite powder in order to separate the cells from the broth. Cells were extracted with polar solvent which was followed by evaporation of the solvent under reduced pressure to obtain a semisolid residue. The residue was treated with dichloromethane with stirring to a solid which was filtered to give (+) catechin as amorphous solid (yield 0.27%).

Advantages

1) Large scale production of (+) catechin through in vitro callus and suspension cultures with yield of 0.3% which is significantly better to the reported yield per unit time.
2) The above process of the invention provides an alternative source of the compound thereby sparing the mature trees from being exploited.
3) Following the process of the present invention (+) catechin can be obtained as a single entity in the cell cultures of *Taxus wallichiana* in contrast to earlier reports of production of a mixture of many related phenolic compounds (e.g. (–) epicatechin-3-O-gallate, (–) epicatechin, gallocatechin) along with (+) catechin from cell cultures of other plants.
4) *Taxus wallichiana* generally grows at the high altitudes of Himalayan belt, hence to obtain the compound from such geographical locations is really difficult while the in vitro production and extraction protocol ensures convenient source of supply.

5) The isolation process to get the compound is very simple which does not need any chromatographic column. Thus, the process would be cost effective and adaptable to large scale production.

What is claimed is:

1. A non-chromatographic process for the production of an isolated, biologically active phenolic compound (+)-catechin of formula

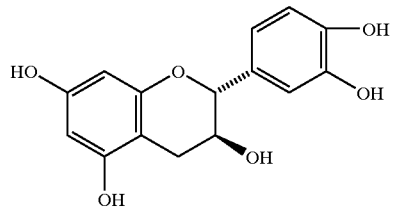

from *Taxus wallichiana* tissue cultures, said process comprising the steps of:
   (a) inoculation of *Taxus wallichiana* explants on a culture medium supplemented with combinations of auxins and cytokinins to prepare the tissue cultures;
   (b) incubation of the tissue cultures under continuous light or dark conditions for 4–6 weeks for callus initiation followed by subculturing at 4–6 week intervals;
   (c) extraction of resultant fresh pulverized calli with at least one polar solvent at room temperature;
   (d) evaporating the at least one solvent to obtain a residuel; and
   (e) treatment of the residue with a chlorinated solvent and isolation of the (+)-catechin compound by filtration.

2. A process as claimed in claim 1 wherein the explants used to initiate calli are selected from the group consisting of needles, twigs, stem segments devoid of needles and seeds of *Taxus wallichiana*.

3. A process as claimed in claim 1 wherein the culture medium is selected from the group consisting of Murashige and Skoog's medium; Gamborg's B5 medium, White's medium, and Nitsch-and Nitsch's basal medium.

4. A process as claimed in claim 3 wherein the auxins are selected from the group consisting of Indole acetic acid, naphthalene acetic acid, 2,4-dichlorophenoxy acetic acid, 2,4,6,-trichlorophenoxy acetic acid, Picloram and Indole Butyric Acid.

5. A process as claimed in claim 3 wherein the cytokinins are selected from the group consisting of 6-benzyl amino purine, 6-methyl aminopurine, 2-isopentenyl amino purine, kinetin, zeatin, and thiadiazuron.

6. A process as claimed in claim 3 wherein the concentration of auxin in the medium is about 1–5 mg/l.

7. A process as claimed in claim 3 wherein the concentration of cytokinin in the medium is about 0.1 to 1 mg/l.

8. A process as claimed in claim 3 wherein the culture medium is Murashige and Skoog's medium comprising $NH_4NO_3$ 1,650 mg/l, $KNO_3$ 1,900 mg/l, $CaCl_2.2H_2O$ 400 mg/l, $MgSO_4.7H_2O$ 370 mg/l, $KH_2PO_4$ 170 mg/l, $Na_2EDTA.2H_2O$ 7.2 mg/l, $FeSO_4.7H_2O$ 27.8 mg/l, $MnSO_4.4H_2O$ 22.3 mg/l, $ZnSO_4.7H_2O$ 8.6 mg/l, $H_3BO_3$ 6.2 mg/l, KI 0.83 mg/l, $Na_2MoO_4.2H_2O$ 0.25 mg/l, $CuSO_4.5H_2O$ 0.025 mg/l, $CoCl_2.6H_2O$ 0.025 mg/l, Glycine 2.0 mg/l, Nicotinic acid 0.5 mg/l, Pyridoxine HCl 0.5 mg/l, and Thiamine HCl 0.1 mg/l.

9. A process as claimed in claim 3 wherein the culture medium is Gamborg's B5 medium comprising $KNO_3$ 3,000 mg/l, $(NH_4)_2SO_4$ 134 mg/l, $MgSO_4.7H_2O$ 500 mg/l, $CaCl_2.2H_2O$ 150 mg/l, $NaH_2PO_4.H_2O$ 150 mg/l, $MnSO_4.H_2O$ 10.0 mg/l, KI 0.75 mg/l, $H_3BO_3$ 3.0 mg/l, $ZnSO_4.7H_2O$ 2O 2.0 mg/l, $CuSO_4$ 0.025 mg/l, $NaMoO_4.2H_2O$ 0.25 mg/l, $CoCl_2.6H_2O$ 0.025 mg/l, $Na_2EDTA.2H_2O$ 37.2 mg/l, and $FeSO_{4.7}H_2O$ 27.8 mg/l.

10. A process as claimed in claim 3 wherein the culture medium is White's medium comprising $Ca(NO_3)_2$ 142.0 mg/l, $KNO_3$ 81.0 mg/l, $MgSO_4.7H_2H_2O$ 70.0 mg/l, KCl 65.0 mg/l, $KH_2PO_4$ 12.0 mg/l, and $(FeSO_4)_3$ 2.46 mg/l.

11. A process as claimed in claim 3 wherein the culture medium is Nitsch and Nitsch's medium comprising $NH_4NO_3$ 20.0 mg/l, $KNO_3$ 950 mg/l, $H_3BO_3$ 10.0 mg/l, $KH_2PO_4$ 68.0 mg/l, $Na_2MoO_4.2H_2O$ 0.143 mg/l, $CaCl_2$ 41.5 mg/l, $MgSO_4.7H_2O$ 185 mg/l, $MnSO_4.4H_2O$ 15.0 mg/l, $ZnSO_4.H_2O$ 10.0 mg/l, $CuSO_4$ 0.14 mg/l, $FeSO_4$ 111.4 mg/l, $Na_2EDTA$ 149 mg/l, Biotin 0.05 mg/l, Glycine 2.0 mg/l, Nicotinic acid 5.0 mg/l, Pyridoxine HCl 0.5 mg/l, Thiamine HCl 0.5 mg/l, and Folic acid 5.0 mg/l.

12. A process as claimed in claim 1 wherein the tissue cultures are incubated under continuous light of 300–3000 lux or under continuous dark conditions.

13. A process as claimed in claim 1 further comprising the step of harvesting the explants at different growth intervals wherein the culture harvesting time ranges from one month to thirty six months.

14. A process as claimed in claim 1 wherein the polar solvent for extraction of the callus is selected from the group consisting of methanol, ethanol, propanol and butanol.

15. A process as claimed in claim 1 wherein the ratio of auxin and cytokinin is between 6 to 20:1.

16. A process as claimed in claim 1 wherein the medium is supplemented with casein hydrolysate in an amount ranging between 100–400 mg/l.

17. A process as claimed in claim 1 wherein ascorbic acid is used for prevention of phenolic leaching into the medium in the range between 10–50 mg/l.

18. A process as claimed in claim 1 wherein the chlorinated solvent used is selected from the group consisting of chloroform and dichloromethane.

* * * * *

UNITED STATES PATENT AND TRADEMARK OFFICE
CERTIFICATE OF CORRECTION

PATENT NO. : 6,620,599 B1
DATED : September 16, 2003
INVENTOR(S) : Chattopadhyay et al.

It is certified that error appears in the above-identified patent and that said Letters Patent is hereby corrected as shown below:

<u>Column 6,</u>
Line 4, add a space after "$H_2O$", should read -- $MgSO_4.7H_2O$ 370 mg/1, --
Line 17, delete "2O" should read -- ZnSO4.7H2O 2.0 mg/1, --
Line 18, add a space after "H2O", should read -- NaMoO4.2H2O 0.25 mg/1. --

Signed and Sealed this

Twenty-eighth Day of October, 2003

JAMES E. ROGAN
*Director of the United States Patent and Trademark Office*